United States Patent [19]

Serwer

[11] Patent Number: 4,693,804
[45] Date of Patent: Sep. 15, 1987

[54] APPARATUS FOR BIDIMENSIONAL ELECTROPHORETIC SEPARATIONS

[75] Inventor: Philip Serwer, San Antonio, Tex.

[73] Assignee: Board of Regents, The University of Texas System, Austin, Tex.

[21] Appl. No.: 684,275

[22] Filed: Dec. 19, 1984

[51] Int. Cl.⁴ ............................................ G01N 27/26
[52] U.S. Cl. ............................ 204/182.1; 204/299 R; 204/182.8
[58] Field of Search .............. 204/182.8, 299 R, 182.1

[56] References Cited

U.S. PATENT DOCUMENTS

| | | | |
|---|---|---|---|
| 3,567,611 | 3/1971 | Michel et al. | 204/182.8 |
| 3,865,712 | 2/1975 | Davies | 204/299 R |
| 3,888,759 | 6/1975 | Elson et al. | 204/299 |
| 3,930,973 | 1/1976 | Nerenberg | 204/182.8 |
| 3,988,230 | 10/1976 | Krotz | 204/182.8 |
| 4,088,561 | 5/1978 | Anderson | 204/299 R |
| 4,148,703 | 4/1979 | Trop et al. | 204/182.8 |
| 4,294,684 | 10/1981 | Serwer | 204/299 R |
| 4,305,799 | 12/1981 | Schwartz et al. | 204/299 R |
| 4,385,974 | 5/1983 | Shevitz | 204/299 R |

FOREIGN PATENT DOCUMENTS 0105052 6/1983 Japan ................................ 204/182.8

WO84/02001 5/1984 PCT Int'l Appl. ............. 204/299 R

Primary Examiner—John F. Niebling
Assistant Examiner—John S. Starsiak, Jr.
Attorney, Agent, or Firm—Arnold, White & Durkee

[57] ABSTRACT

An apparatus for conducting orthogonal electrophoretic separations in a gel bed. The apparatus comprises two pairs of opposing tanks, each tank having a flat base, an electrode assembly and buffer containment zone. A gel bed may be formed on the base so that each edge of the gel bed is in communication with a buffer containment zone. Each buffer tank may be isolated by a barrier from the base or gel bed. A sample of soluble materials may be placed in the gel bed and electrophoretically driven in a first direction and then in an orthogonal second direction. The barriers are all utilized together to retain liquid gel precursor and then are used in opposing pairs to isolate tanks whose electrode assemblies are not in use.

After the soluble materials have been subjected to electrophoresis in both dimensions, possibly each dimensional migration in a different gel, the gel migration patterns of the materials may be found by staining, for example.

18 Claims, 7 Drawing Figures

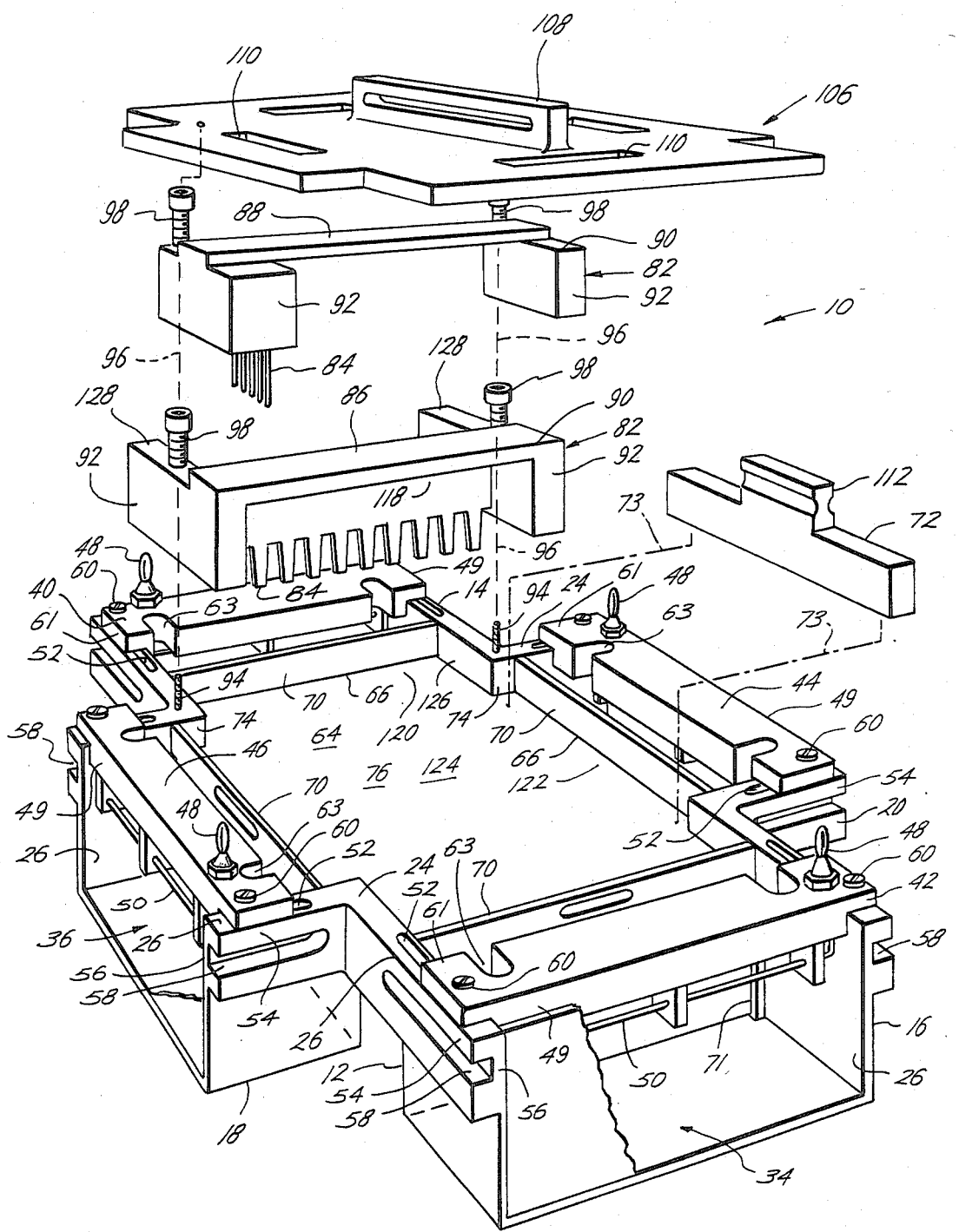

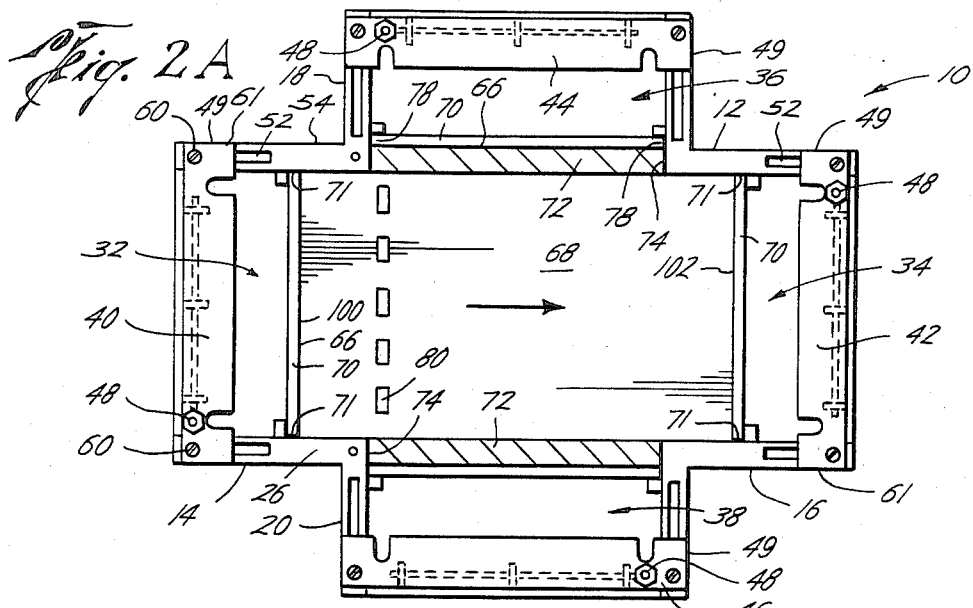
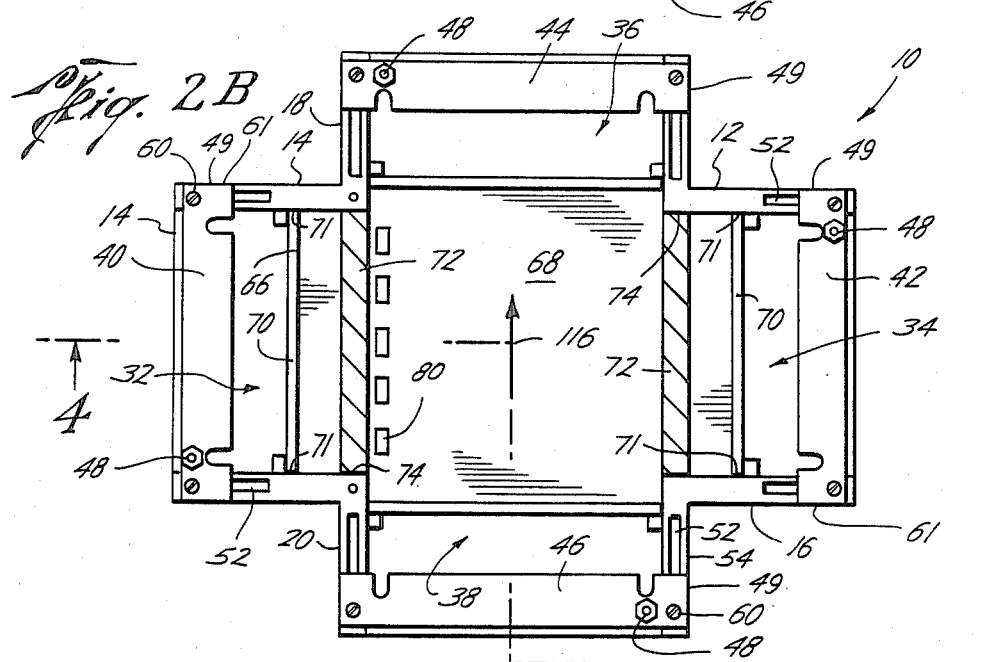
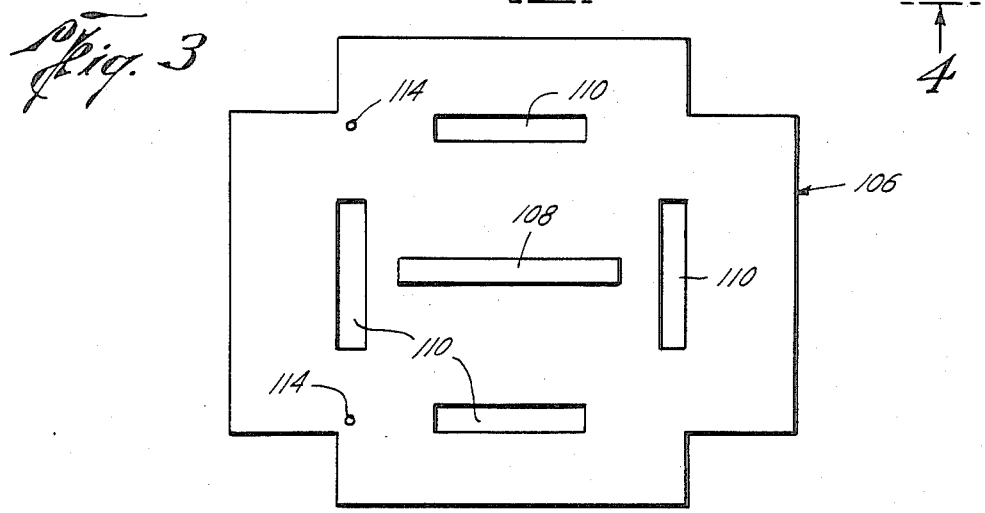

APPARATUS FOR BIDIMENSIONAL ELECTROPHORETIC SEPARATIONS

BACKGROUND OF THE INVENTION

Support for development of the present invention was received from the United States Department of Health, Education and Welfare.

The present invention relates generally to the field of multidimensional electrophoretic analysis and, more particularly, but not by way of limitation, to an apparatus for conducting bidimensional or orthogonal electrophoretic analyses of molecular species in an open flat bed gel.

Molecules or particles having net electrical charges may be distinguished by observing their migrations in suitable media subjected to the application of electrical fields. Such migrations are dependent upon the composition of the media, the nature of the electrical fields and characteristics of the molecules or particles themselves, such as net surface electrical charge, size and shape.

Complex mixtures of, for example, proteins, peptides or nucleic acids have long been analyzed by electrophoresis in various media. Among the more popular media for these analyses have been polyacrylamide and agarose gels containing an electrically conductive pH buffer.

Both columnar and slab electrophoretic apparati have been utilized for gel electrophoresis of various molecules. Unidimensional gel electrophoretic separation procedures are well known. Numerous approaches have been made toward establishing reproducible procedures for bidimensional gel electrophoretic separations of molecules. Most popularly, these approaches have involved electrophoretic separation in a vertical columnar gel, particularly polyacrylamide, followed by extraction of the gel column. The extracted columnar gel, bearing molecules separated along its length, has been then embedded in a gel slab having different characteristics such as pH, porosity or denaturant content, for example. An electric field generally perpendicular to the embedded gel was then applied to cause a molecular migration orthogonal to the original electric field applied to the columnar gel. This approach to bidimensional electrophoretic analysis is subject to several difficulties. First, the physical manipulations required to extract the columnar gel from its retaining column often result in gel deformation or breakage. For an intact columnar gel to be extractable at all from a column, the gel medium must have sufficient tensile strength to withstand handling. Experience has shown desirable gel media such as, for example, 0.3 to 0.4% agarose gels, cannot be extracted from a gel column without breakage. Because an extracted columnar gel, particularly a gel with low gel content, is difficult to embed in a precise linear orientation, further irreproducibility of migrations in the second electrophoretic dimension may arise.

In U.S. Pat. No. 4,385,974, issued to Shevitz a slab gel bidimensional electrophoresis apparatus is described. This apparatus included two pairs of opposing tanks, electrode means in each tank and means for supporting a gel slab defined by the space between a pair of parallel gel plates, a pair of barrier webs and two gels.

SUMMARY OF THE INVENTION

The present invention comprises an apparatus for conducting orthogonal electrophoretic analyses in an opn horizontal flat bed gel. The apparatus includes a base and a first pair and second pair of opposing tanks. Each tank has a buffer containment zone. The apparatus further includes means for supporting a gel bed on said base between the tanks and in communications with the buffer containment zones. The apparatus further comprises an electrode assembly for conducting electricity to each buffer containment zone and means for isolating the buffer containment zones from the gel bed.

BRIEF DESCRIPTION OF THE DRAWINGS

FIG. 1 is an exploded isometric and partial cutaway view of an embodiment of the apparatus of the present invention.

FIG. 2A is a plan view of a partially assembled embodiment of the apparatus of the present invention with a gel.

FIG. 2B is a plan view of a partially assembled embodiment of the apparatus of the present invention with a gel.

FIG. 3 is a plan view of the cover for an embodiment of the apparatus of the present invention.

DETAILED DESCRIPTION OF THE PREFERRED EMBODIMENT OF THE PRESENT INVENTION

Figure 4:
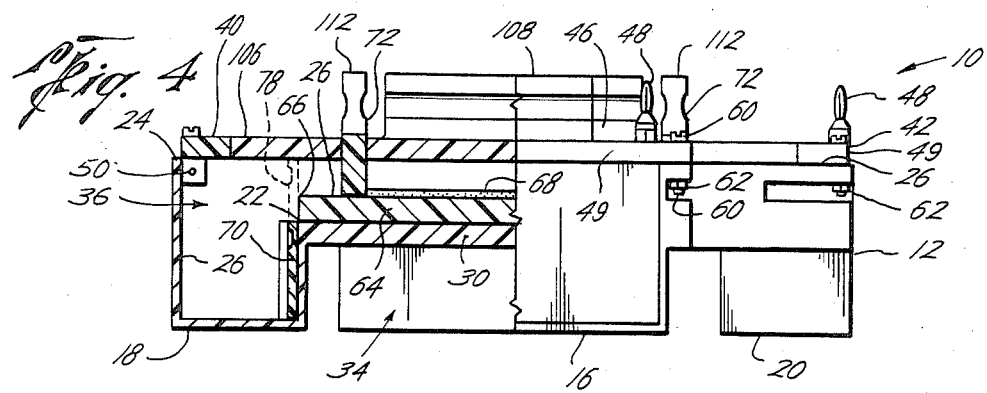
FIG. 4 is an elevational and partial sectional view of an embodiment of the apparatus of the present invention.

In one aspect the invention concerns a method of performing multi-dimensional electrophoretic analysis wherein two different gel bodies abut one another. A solution of the substance to be analyzed is subjected to an electrical field which drives the substance in a first direction through one of the bodies. The travel path in this instance is adjacent the second gel body. Following this step, a second electrical field is applied in a second and different direction, generally orthogonal to the first direction, to drive the substance into the adjacent second gel body. The substance need not be removed or altered in the process; nor need any fluids be withdrawn or replaced during the process.

In a second aspect the invention concerns an apparatus for conducting multi-dimensional electrophoretic analysis. The apparatus comprises a substantially flat base for supporting a bed of a first gel. The flat base is surrounded by four tanks, one on each side, adapted to contain a buffer solution. The juxtaposition of the tanks relative to the flat base is such that the bed of gel on the flat base can be covered by fluid overflowing from one or more of the tanks. Barriers are provided to interrupt such flow as desired. An electrode is positioned in each tank, and is in a common circuit with the electrode in the tank on the opposite side of the base plate through the buffer fluid superposed on the flat base.

Special forms such as combs and elongated bars are provided to define wells, trenches and similar cavities in a bed of gel formed on the flat base. A second gel can then be formed on the flat base in such a cavity to abut the first gel. A liquid suspension of a substance to be studied can then be placed in contact with the second gel to be driven electrophoretically and sequentially through the two gels. To establish electrical circuits through the gels, buffer solution is flowed from the tanks over the two gels and into contact with the substance.

The performance of orthogonal electrophoretic analyses is facilitated with an apparatus generally designated by the numeral 10 in FIGS. 1, 2A, 2B and 4. The apparatus 10 is preferably constructed of Plexiglas (thermoplastic poly (methyl methacrylate), Rohm & Haas Co., Independence Mall West, Philadelphia, Pa. 19105). The apparatus 10 has a base 12 which has a first pair of opposing tanks 14 and 16 and a second pair of opposing tanks 18 and 20. Each tank 14, 16, 18 and 20 has a front rim 22, an upper rim 24 and walls 26. The base 12 also has a baseplate 30 which may be integrally connected or formed with the front rim 22 of each tank 14, 16, 18 and 20. The base 12 is adapted to contain a liquid in communication with both pairs of opposing tanks 14, 16, 18 and 20.

Each tank 14, 16, 18 and 20 has a buffer containment zone 32, 34, 36 and 38. Electrode assemblies 40, 42, 44 and 46 are removably and slidably attached to the upper rim 24 of each tank 14, 16, 18, and 20. The electrode assemblies 40, 42, 44 and 46 each have an electrical input connector 48, in this embodiment a banana plug, mounted on the electrode assembly body 49. Each electrical input connector 48 is connected to an electrode 50, in this embodiment a wire comprising platinum. Each electrode 50 is disposed within a buffer containment zone 32, 34, 36 and 38 for the passage of an electrical current thereto. Each electrode assembly 40, 42, 44 and 46 is movably attached to the upper rim 24 of a tank 14, 16, 18 and 20. This movable attachment is facilitated by a slot 52 through the upper portion 54 of the base wall 56 extending to a groove 58 in the wall 56. A bolt 60 extends through a perforation (not shown) at each end 61 of every electrode assembly body 49, through the slot 52 where it is threadedly attached to a nut 62 in the groove 58. The electrode assemblies 40, 42, 44 and 46 may thus be attached to the base 12 at any desired distance from the baseplate 30. Openings 63 in the electrode assembly body 49 may be used for insertion of thermometers or other monitoring devices if desired.

The apparatus 10 preferably comprises a removable gel platen 64. The gel platen 64 is removably emplaced in the apparatus 10 upon the baseplate 30 and is most preferably cross-shaped as shown most clearly in FIG. 1. The gel platen 64 has edges 66 in proximity to the front rim 22 of each tank 14, 16, 18 and 20.

Other components of the apparatus 10 are most clearly described in the context of their usage. Orthogonal flat bed gel electrophoreses in the apparatus of the present invention of course require a gel bed 68 as seen in FIGS. 2A, 2B, 4, 5 and 6. A gelable liquid such as a warm agarose solution or an acrylamide -N,N'methylenebisacrylamide mixture, for example, is prepared by wellknown methods. The gel platen 64 is placed in the apparatus 10 and barriers are emplaced to contain the gelable liquid when it is poured upon the gel platen 64. These barriers, which are preferably electrically insulative, may be slidable plates 70 or blocks 72. The blocks 72 are shaped to fittingly engage a portion 74 of the base wall 56 and the upper surface 76 of the gel platen 64. The broken lines 73 in FIG. 1 schematically indicate appropriate block 72 placement on the platen surface 76. The slidable plates 70, all shown in FIG. 1 in raised position, are slidably mounted in grooves 71 on the tank walls 26. The slidable plates 70 may be raised as shown in FIG. 1 and by dashed lines 78 in FIG. 4, when they fittingly engage an edge 66 of the gel platen 64 and walls 26. The gelable liquid is poured onto the surface 76 of the gel platen 64, and either emplaced blocks 72 or upwardly oriented 78 slidable plates 70 may be used to contain the gelable liquid until gelling has occurred and the gel bed 68 has stabilized. The term "gel bed" as used herein is defined as the bed of gel or gel itself to be used as the electrophoretic medium. Use of the slidable plates 70 results in a cross-shaped gel bed 68 and use of the blocks 72 results in a rectangular gel bed 68. The shape of the gel bed 68 may be created as desired by use of the blocks 72 alone, the slidable plates 70 alone, or in any combination. However, to maintain a uniform field, the blocks 72 should be used to produce a rectangular gel.

To exclude the gelable liquid from particular positions, these positions to become wells 80 in the gel bed 68, sample well forming combs 82 are utilized. These combs 82 have teeth 84 which are preferably tapered (only one of which is numerically marked on each comb 82). The combs 82 may have teeth of different shape and arrangement, as exemplified by comparing the teeth 84 of first comb 86 and the second comb 88, for production of wells 80 having different locations, sizes and spatial arrangements. Each comb 82 has a support structure 90. The support structures 90 include walls 92 having alignment perforations (not shown) adapted to receive vertically disposed guide pins 94 mounted on the upper portion 54 of the base wall or rim 56. Engagements of the combs 82 with the guide pins 94 are schematically indicated by broken lines 96. Threadedly mounted above the alignment perforations (not shown) are extraction bolts 98 shown in withdrawn position. When a well-forming comb 82 is to be removed from the apparatus 10, the extraction bolts 98 are each screwed downward to press against the guide pins 94 and lift the well-forming comb 82.

In preparation of a uniform gel bed 68, the gel platen 64 is emplaced, and the blocks 72 and/or slidable plates 70 are positioned to retain the gelable liquid. A well-forming comb 82 is emplaced over the guide pins 94 and the gelable liquid is poured onto the gel platen to a depth generally between about 2 and about 10 mm immersing segments of the teeth 84. After gelling has occurred, generally in a period less than an hour, the comb 82 may be removed by downwardly screwing the extraction bolts 98 although this removal is preferably done after gel bed 68 immersion in buffer. The tanks 14, 16, 18 and 20 are filled with a suitable electrophoresis buffer until the gel bed 68 is covered by at least 2 to 4 mm of electrophoresis buffer and the electrodes 50 are substantially immersed.

Materials to be electrophoretically analyzed are dissolved in a suitable solution having high density from, for example, sucrose or dextran included at a concentration of at least about 2.5% w/v. A volume of the solution less than the volume of a sample well 80 as shown in FIG. 2A is placed in a selected sample well 80. The apparatus cover 106 with a a handle 108 and slots 110 for insertion of block handles 112 is used to cover the apparatus 10 during electrophoresis. The cover 106 has alignment perforations 114 for slidingly engaging the guide pins 94. Electrophoresis is then performed in a first dimension as follows. The slidable plates 70 are slidingly inserted downward, or the blocks 72 are removed at the first pair of opposing tanks 14 and 16 and the slidable plates 70 or blocks 72 are left at place in the second pair of opposing tanks 18 and 20. A source of direct electrical current is attached to the electrical input connectors 48 of the first pair of opposing tanks 14 and 16. The slidable plates 70 or blocks 72 remaining at the second pair of opposing tanks 18 and 20 largely prevent the passage of electricity through their corresponding buffer containment zones 36 and 38. The passage of electricity through the buffer containment zones 32 and 34, each in communication with an end 100, 102 of the gel bed 68 results in a voltage gradient and the migration of materials in the directions indicated by the arrow 104 in FIG. 2A.

After a suitable period of electrophoresis as described above, the materials migrate in the gel bed 68 to a desired distance, depending on their size, shape and net electrical charge as well as the pH of the electrophoresis buffer, the presence or absence of denaturants and the intensity of the voltage gradient. The source of electricity is deactivated and disconnected from the electrical input connectors 48 of the first dimension electrode assemblies 40 and 42 and is then reconnected to the input connectors 48 of the second dimension electrode assemblies 44 and 46. The slidable plates 70 or blocks 72 are removed from their blocking positions at the second pair of opposing tanks 18, 20 and the buffer containment zones 32 and 34 of the first pair of opposing tanks 14 and 16 are blocked by slidable plates 70 or blocks 72.

Electrophoresis in the second dimension, orthogonal to the first dimension, is then commenced by reactivation of the electrical source. Material migration occurs in the direction designated by the arrow 116 in FIG. 2B. After electrophoresis in this second dimension for a period to allow sufficient material migration, the electrical source is deactivated and the cover 106 is removed. The gel platen 64 and overlying gel bed 68 are then removed from the apparatus 10. The migratory location of materials in the gel bed 68 may then be determined directly, for example by staining, or the gel may be first processed. Processing may include gel drying, solvent immersion, staining, radioautography, alone or in various combinations, for example.

In many cases it is desirable to conduct the first dimension electrophoresis in a gel different from the gel of the second dimensional electrophoresis. This type of differential orthogonal electrophoresis is readily accomplished with the apparatus 10 of the present invention. The inclusion of a second gel medium, particularly for the first dimensional electrophoresis is facilitated by utilizing a template such as that described in U.S. Pat. No. 4,294,684, issued to Serwer, which is incorporated by reference herein.

The template optimally useful in electrophoresis performed according to the present invention has two elongate bars securely attached to a support frame. The support frame fittingly engages within the cavity 118 of the first well-forming comb 86 so that the elongate bars flushly abut the teeth 84. The bars are preferably made of Teflon (tetrafluorethylene fluorocarbon polymers, DuPont de Nemours E. I. & Co., Wilmington, Del. 19898) or Delrin (thermoplastic acetal resin, DuPont de Nemours E. I. & Co.). The template and the comb 86 are emplaced over the gel platen 64 and the gel platen 64 is enclosed by the slidable plates 70 or blocks 72 as described earlier.

A first gelable liquid is then poured onto the enclosed gel platen 64 and allowed to gel. The comb 86 and template are then removed leaving wells 80 and two trenches (not shown). The comb 86 but not the template is replaced in contact with the gel platen 64 and a second gelable liquid, precursor to a second gel having characteristics different from the first gel is added to the trenches in the gel bed 68 left by the template. After gelling, the comb 86 is removed and the sample added to sample well 80 in the second gel, as shown most clearly in FIG. 5. The orthogonal electrophoresis, conducted as earlier described, now occurs in a different gel for each dimension.

The apparatus 10 may be designed to contain more than one gel platen 64. Additional gel platens (not shown) of similar designs may be mounted, each vertically spaced a distance apart from each other and from the lowermost platen 64 so that their edges (not shown) are in proximity to the buffer containment zones 32, 34, 36 and 38. In this manner, with appropriate modifications, for example, in the gel bed 68 forming procedures, sample addition procedures, the sizes of the blocks 72 the level of buffer additions and the amount of electrical current provided to the electrode assemblies 40, 42, 44 and 46, analyses in multiple gel beds 68 may be simultaneously performed.

In addition, alterations may be made in the numbers of orthogonal electrophoretic analyses done in a single gel bed. For example, multiple first dimensional gel beds 142 may be contained in the second dimensional gel bed 144. These first dimensional gel beds 142 need be spaced apart at a distance sufficient to preclude overlapping patterns of material migration.

To more fully describe the structure and uses of the present invention, the following exemplifications, not intended as limitations unless otherwise specifically indicated herein, are included.

EXAMPLE 1

Materials and Methods

Bacteriophage and Bacterial Strains

The source and preparation of the mature DNA's of bacteriophages T4, T5 and T7 have previously been described (Serwer, P. (1980) Biochemistry 19, 3001-3004). The DNA of bacteriophage deletion mutant $\pi 590$ (referred to as $\lambda 590$) was obtained and converted to open circles, as previously described (Serwer, P. and Allen J. L. (1984) Biochemistry 23, 922-927). Bacteriophage P22 (referred to as P22) and P22 without tail spikes (tail spikes are the product of P22 gene 9 (Casjens, S. and King, J. (1974) J. Supramol. Struct. 2, 202-204); P22 without the product of gene 9 is referred to as $9^--P22$) were purified preparations. Bacteriophage T7 without its tail fibers ($17^-$T7) was purified as previously described (Serwer, P. and Hayes, S. J. (1982) Electrophoresis 3, 76-80).

Buffers and Reagents

Bacteriophages were stored in Tris/Mg buffer: 0.2 M NaCl, 0.01 M Tris-Cl, pH 7.4, 0.001 M $MgCl_2$. Electrophoresis buffer A was: 0.05 M sodium phosphate, pH 7.4, 0.001 M $MgCl_2$; electrophoresis buffer B was 0.05 M sodium phosphate, pH 7.4, 0.001 M EDTA. Sample buffer A was 0.005 M sodium phosphate, pH 7.4, 0.001 M $MgCl_2$, 4% sucrose, 400 ug/ml bromophenol blue. Sample buffer B was 0.005 M sodium phosphate, pH 7.4, 0.001 M EDTA, 30% sucrose, 400 ug/ml bromophenol blue. Seakem ME and HGT[P]preparations of agarose were obtained from the Marine Colloids Division of the FMC Corporation (Rockland, ME)

Electrophoresis Apparatus

An electrophoresis apparatus 10 as shown in FIGS. 1, 2A, 2B and 4 for two-dimensional electrophoresis in submerged, horizontal gels was constructed as follows. The gel platen 64 was a 1.3 cm (½ inch) thick piece of Plexiglas, shaped like a cross that has two perpendicular arms 120 and 122 (FIG. 1) of different length. The arms 120 and 122 met at their centers 124 so that the cross shape had two-fold rotational symmetry. The longer arm 120 was 21.9 cm long and 13.3 cm wide. The shorter arm 122 was 15.8 cm long and 15.0 cm wide. At both ends of the longer arm 120 was attached a tank (Tanks 14 and 16 in FIG. 1) 7.0 cm high (vertical dimension)×13.3 cm wide×6.6 cm deep, made of Plexiglas. At both ends of the shorter arm 122 was attached a tank (Tanks 18 and 20 in FIG. 1) 7.0 cm high×15.0 cm wide×6.4 cm deep. Walls 126 surrounding the gel platen 64 were made of 1.3 cm thick Plexiglas and extended 2.0 cm above the base of the platen 64.

Electrophoresis in the first dimension was performed using the electrode assemblies 40 and 42 in the first pair of tanks 14 and 16. To prevent electrical current from entering the second pair of tanks 18 and 20 during electrophoresis in the first dimension, 1.3 cm thick Plexiglas blocks 72 were used to extend the gel bed walls before the second pair of tanks 18 and 20. A second set of Plexiglas blocks 72 (not shown) was similarly used to prevent electrical current from entering the first pair of tanks 14 and 16 during the second electrophoresis. The Plexiglas blocks 72, machined to a tolerance of 0.2 mm, were held in place by friction.

Slidable Plexiglas electrode assemblies 40, 42, 44 and 46 held platinum electrodes 50 in the tanks 14, 16, 18 and 20, as previously described (Serwer, P. (1983) Electrophoresis 4, 227-231). Connection with the power supply was made through a banana plug electrical input connector 48.

Sample Well-Forming Combs

To form sample wells 80, two different sample well-forming, Plexiglas combs 82 were built. The second comb 88 (FIG. 1) had teeth 84 for forming five sample wells 80, each 2.0 mm×2.0 mm in cross-section. The teeth 84 were on a line parallel to the direction of the first electrophoresis. On both sides of this comb 88 were alignment perforations (not shown) which fitted snugly over the guide pins 94 on the upper portion 54 of the base wall or rim 56 of the electrophoresis apparatus 10. Extraction bolts 98 threaded above these perforations were used to gently lift the comb out of the gel. When the bolts 98 were turned into the holes, they contacted the guide pins 94 and thus lifted the comb 88.

The first comb 86 was a modification of a comb 82 previously used in pouring multiple-concentration agarose gels (Serwer, P. (1984) Methods in Enzymology, in press). As shown in FIG. 1, the comb 86 had extensions 128 that rest on the sides of the electrophoresis apparatus 10 to prevent tipping of the comb 86 during pouring of gelable liquids. This comb 86 had nine tapered teeth 84 and alignment perforations (not shown) with extraction bolts 98; the perforations fit snugly over the same guide pins 94 used with the comb 88. Only one well 80 formed by one of the teeth 84 was used in the experiments presented here.

Pouring Agarose Gels

To pour an agarose gel bed 68 with a single agarose concentration: (a) The second comb 88 was placed in the electrophoresis apparatus 10. (b) Blocks 72 were used to separate the gel platen 64 from the tanks 18 and 20 to be used for the second electrophoresis. (c) The entrances to the tanks 14 and 16 to be used for the first electrophoresis were also obstructed by blocks 72. (d) Agarose in electrophoresis buffer at 50°-55° C. was poured into the gel platen 64 at room temperature (22°-28° C.).

After allowing gelation for 45-50 min, the gel bed 68 and all of the four tanks 14, 16, 18 and 20 were filled with electrophoresis buffer until the buffer level was 2-4 mm above the top of the gel bed 68. After an additional 10-15 min, the slidable Plexiglas plates 70 were lowered below the level of the gel bed 68 and the second comb 88 was removed from the gel by threading the bolts 98 downward.

It is sometimes desirable to use for the second electrophoresis a gel with an agarose concentration different from that of the first dimension gel. This is done by embedding the first dimension gel within the gel to be used for the second electrophoresis, as follows. (a) The first comb 86 was emplaced in the apparatus 10 together with a template that excludes agarose from the space that the first dimension gel will occupy (see U.S. Pat. No. 4,294,684). (b) After pouring the gel for the second electrophoresis around the template and comb 86, gelling was allowed to occur and the template and comb were removed from the gel bed. The trench left by the template was cleaned, the comb 86 was replaced in the gel and the first dimension gel was poured in this trench, as described above. A second trench (not shown) left by the template was filled with gel but not used. After 45-50 min of gelation, buffer was placed in the electrophoresis apparatus 10 and the comb 86 was removed from the gel 10-15 min later, as described above. The template used was made of Plexiglas although the bars are preferably Delrin (thermoplastic acetal resin; DuPont de Nemours, E. I. & Co., Wilmington, Del. 19808) or Teflon (tetrafluoroethylene fluorocarbon polymers; DuPont de Nemours, E. I. & Co., Wilmington, Del. 19808) and had the design of the nine bar template previously described in U.S. Pat. No. 4,294,684 and P. Serwer (1981) Anal. Biochem. 112, 351-356, but had only two of nine bars of the previous template. A first bar was used to form the trench for the first dimension gel and the last bar was present to prevent tipping of the template.

Electrophoresis

For two-dimensional electrophoresis with the same agarose concentration in both dimensions as shown in FIG. 6A and FIG. 6B, the sample well 80 designated by the letter S formed in a uniform gel bed 68 by a tooth 84 of the second well-forming comb 88 was loaded with the sample to be analysed. The first electrophoresis was then conducted at room temperature (25+3° C.), as previously described (Serwer, P. (1981) Anal. Biochem. 112, 351-356). During the first electrophoresis, the second pair of opposing tanks 18 and 20 was obstructed by blocks 72. For the second electrophoresis: (a) The blocks 72 obstructing the second pair of tanks 18 and 20 were removed and the first pair of tanks 14 and 16 was then obstructed with another pair of blocks 72. (b) The power source was disconnected from the first pair of electrode assemblies 40 and 42 and was reconnected to the second pair of electrode assemblies 44 and 46. (c) Additional samples used as markers were placed in sample wells 80 designated by numerals 1 and 2 and adjacent to the sample well 80(s) used for the sample subjected to first electrophoresis. The second electrophoresis was then performed as described above.

For two-dimensional electrophoresis using a first dimension gel more dilute than the gel used for the second electrophoresis, an embedded first dimension gel 142 (See FIG. 5) was used and the procedure for electrophoresis was the same as the procedure described above. For fractionating DNA, the voltage gradient for the second electrophoresis was different from the voltage gradient for the first electrophoresis, as described below.

Staining

To detect bacteriophage-associated DNA in agarose gel beds 68, the DNA was released from the bacteriophage capsid by soaking the gel bed 68 in acetic acid and the gel bed 68 was then stained with ethidium bromide, as previously described (Serwer, P. and Hayes, S. J. (1982) Electrophoresis 3, 76–80). To detect unassociated DNA in agarose gels, the gel was stained with ethidium bromide, as previously described (Serwer, P. (1980) Biochemistry b 19, 3001–3004).

EXAMPLE 2

Results

Determination of Particle Heterogeneity

In preliminary experiments, it was found that during agarose gel electrophoresis bacteriophage P22 formed bands broader than the bands formed by 9−P22 (both migrate toward the anode; data not shown). To determine whether or not irreversible variability in the electrophoretic mobility (u) of bacteriophage P22 caused the greater band width of P22, two-dimensional electrophoresis was performed with P22 and 9−P22 in a gel bed 68 with a single agarose concentration. 9−P22 formed a band 130 (FIGS. 6A and 6B) with a circular profile, but P22 formed a band 132 with an ellipsoidal profile shown in FIG. 6B. 17−T7 formed a band 134 with generally circular profile in the two-dimensional electrophoresis shown in FIGS. 6A and 6B. Thus, in contrast to 17−T7 and 9−P22, the P22 particles migrating comparatively rapidly during the first electrophoresis also migrated comparatively rapidly during the second electrophoresis. The conclusion drawn is that P22 particles are heterogeneous in u. The absence of u heterogeneity for 9−P22 suggests that the cause of the u heterogeneity for P22 is variability in the number of tail spikes.

The conditions for the electrophoretic analyses presented in FIGS. 6A and 6B and discussed above were as follows. A 0.45% Seakem HGT[P] agarose, two-dimensional gel in electrophoresis buffer A was poured with the second well-forming comb 88. Bacteriophage in Tris/Mg buffer were prepared for electrophoresis by diluting with an equal volume of sample buffer A containing 20 ug/ml DNAase I (to digest DNA that sometimes leaks out of bacteriophages during storage). Twenty-five ul of the mixtures indicated below were subjected either to two-dimensional electrophoresis or to the second electrophoresis only. The first and the second electrophoresis were both performed at 0.96 volts/cm for 12 hr. in electrophoresis buffer A. The gels were stained with ethidium bromide after treatment with acetic acid, as described in the Materials and Methods. The samples subjected to two-dimensional electrophoresis were: (a) 9−22 (3 ug) and 17−T7 (3 ug), (b) P22 (5 ug) and 17−T7 (3 ug). The samples subjected to the second electrophoresis only were: (1) 9−P22 (1.5 ug), (2) 17−T7 (1.5 ug), (3) P22 (2.5 ug). The horizontal arrow 136 (FIG. 6A) indicates the direction of the first electrophoresis (I); the vertical arrow 138 indicates the direction of the second electrophoresis (II). The sample wells 80 used for samples subjected to two-dimensional electrophoresis are indicated in FIGS. 6A and 6B by the letter S. The sample wells 80 used for samples subjected only to the second electrophoresis are indicated by the numerals 1 and 2. The bands resulting from electrophoresis only in the second dimension are designated by the numeral 140.

Separation of Double-Stranded Open DNA Circles from a Mixture of Linear DNA's of Variable Length During electrophoresis in one direction (with non-denaturing conditions) of a mixture of different double-stranded DNA's, variability of u can be caused by variability of DNA molecular weight and (or) variability of DNA conformation (linear, open circular, closed circular, branched) (Bell, L. and Byers, B. (1983) Anal. Biochem. 130, 527–535; Serwer, P. (1980) Biochemistry 19, 3001–3004; and Serwer, P. and Allen, J. L. (1984) Biochemistry 23, 922–927). Thus, unless independently-obtained information about either molecular weight distributions or conformations is considered, a single electrophoresis cannot be used to determine either molecular weights or conformations of heterogeneous molecules in a mixture. However, the dependence of u on agarose concentration and voltage gradient varies with conformation at any molecular weight (Serwer, P. (1980) Biochemistry 19, 3001–3004; and Serwer, P. and Allen, J. L. (1984) Biochemistry 23, 922–927). Thus, two-dimensional electrophoretic systems may be developed to obtain DNA conformation and molecular weight distributions with less additional information than required for single dimensional electrophoreses.

Figure 5:
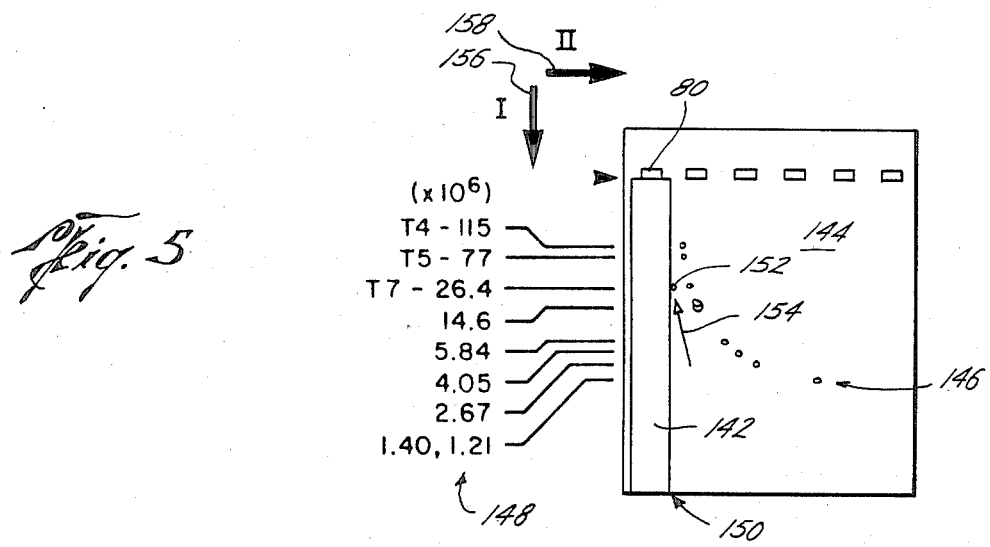
FIG. 5 is a plan view of molecular analysis conducted by orthogonal electrophoresis according to an embodiment of the present invention.
Figure 6:
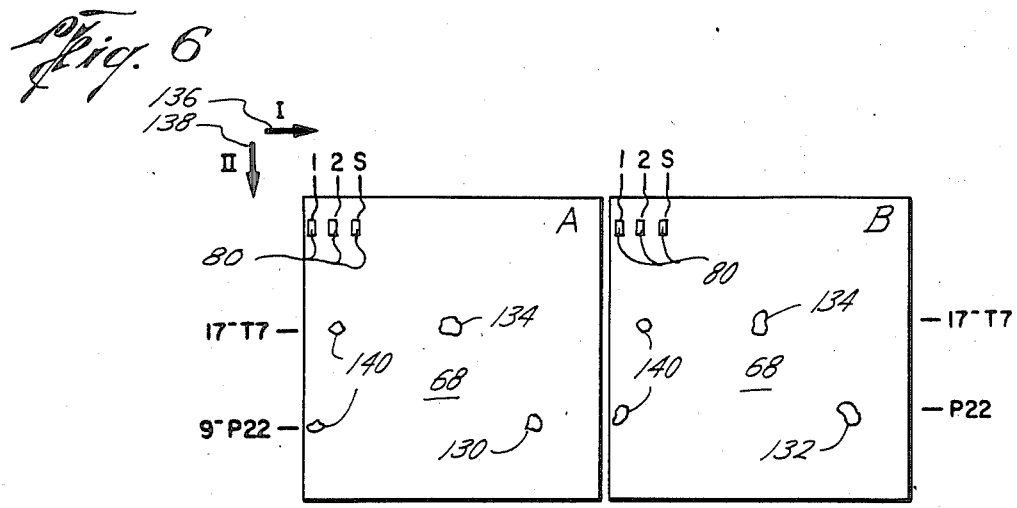
FIG. 6 is a plan view of molecular analyses conducted by unidimensional and orthogonal electrophoresis according to an embodiment of the present invention.

Using data from Serwer et al. (Serwer, P. and Allen, J. L. (1984) Biochemistry 23, 922–927), the following procedure was developed to detect open circular λ590 DNA in the presence of a mixture of linear DNA's as shown in FIG. 5. (a) First dimension electrophoresis of this mixture was performed at 0.34 volt/cm in a first dimensional gel bed 142 of 0.15% agarose; the λ590 open circles comigrated with linear bacteriophage T7 DNA of the same molecular weight ($26.4 \times 10^6$) in the first dimension as previously shown (Serwer, P. and Allen, J. L. (1984) Biochemistry 23, 922–927). (b) Second dimension electrophoresis was performed at 1.0 volt/cm in a second dimension gel bed 144 of 0.7% agarose; the λ590 circles migrated only approximately one third as fast as T7 DNA in the second dimension. As expected (Bell, L. and Byers, B. (1983) Anal. Biochem. 130, 527–535; and Serwer, P. and Allen J. L. (1984) Biochemistry 23, 922–927), the T7 DNA and other linear DNA's were on a continuous curve 146 after this two-dimensional electrophoresis; the molecular weights of the linear DNA's are indicated at the left of FIG. 5 in the column designated by the numeral 148. Also as expected, the λ590 open circle band 152 is on the first dimension gel 142 side 150 of this curve 146 as emphasized by an arrow 154. An experiment similar to this electrophoretic analysis may be used to detect any open circular DNA. However, as the molecular weight of the open circular DNA decreases, it will be necessary to increase the agarose concentration of the gel 144 used for the second electrophoresis (Serwer, P. and Allen, J. L. (1984) Biochemistry 23, 922–927).

The DNA bands (see FIG. 5) in the continuous curve 146, for example, shown in this electrophoretic analysis maintained the shape of bands formed after one-dimensional electrophoresis (Serwer, P. (1980) Biochemistry 19, 3001-3004; and Serwer, P. and Allen J. L. (1984) Biochemistry 23, 922-927). (The band skewing in the direction of the first electrophoresis is caused by a slight sample overloading; see Serwer (Serwer, P. (1980) Biochemistry 19, 3001-3004)). However, the diameters of the bands is less than the length of the sample well 80 used for the first electrophoresis. This latter effect is the result of band compression during passage from the first dimension gel to the more concentrated gel used for the second electrophoresis. This compression increases with increasing molecular weight of linear DNA (as expected (Serwer, P. (1980) Biochemistry 19, 3001-3004)). The narrowing of bands during the second electrophoresis should improve detection sensitivity. However, as bands become narrower they also become increasingly difficult to distinguish from particles such as dust or lint on the gel surface. In cases of ambiguity, it is necessary to visually examine the gel from the side, as well as from the top.

The conditions for the electrophoretic analysis discussed above and shown in FIG. 5 were as follows. A 0.15% Seakem ME first dimension gel 142 in electrophoresis buffer B was embedded within a 0.7% Seakem ME second dimensional gel 144 in electrophoresis buffer B, as described in the Materials and Methods section. A 45 ul mixture of the following DNA's (in 0.1 M NaCl, 0.01 M Tris-Cl, pH 7.4, 0.001 M EDTA) was diluted with 5 ul of sample buffer B and was subjected to electrophoresis at 0.34 volts/cm for 18 hr. in the first dimension gel, as also described in the Materials and Methods section: mature DNA's of bacteriophages T4, T5 and T7 (15-20 ng each), 20 ng of open circular λ590 DNA and a restriction enzyme Hind III digest of 40 ng of wild-type DNA (Wellauer, P. K., Reeder, R. H., Carroll, D., Brown, D. D., Deutch, T., Higashinakagawa, T., and David, I. (1974) Proc. Natl. Acad. Sci., USA 71, 2823-2827). The second (orthogonally oriented) electrophoresis was performed at 1 volt/cm for 7.5 hr. The gel was then stained with ethidium bromide. The vertical arrow 156 indicates the direction of the first electrophoresis (I); the horizontal arrow 158 indicates the direction of the second electrophoresis (II). Only a single well 80 (see FIG. 5) used for the first electrophoresis. The remaining sample wells were not used in this experiment. The molecular weights of the linear DNA's (Wellauer, P. K., Reeder, R. H., Carroll, D., Brown, D. D., Deutch, T., Higashinakagawa, T., and David, I. (1974) Proc. Natl. Acad. Sci., USA 71, 2823-2827; and Serwer, P. (1980) Biochemistry 19, 3001-3004) are indicated in the column marked by the numeral 148. Bands formed by T7, T5 and T4 DNA's are indicated next to their molecular weights; the band 152 of open circular λ590 DNA is indicated by the arrow designated by numeral 154. The remaining bands formed by linear DNA are from the restriction enzyme Hind III digest of wild-type DNA.

EXAMPLE 3

Discussion of Results

The procedure discussed above relating to FIG. 6A and 6B can be routinely used for determining whether or not variability in u exists for particles that form a single band during agarose gel electrophoresis. This procedure is analogous to a two-dimensional procedure in which a columnar first dimension gel is used and is subsequently embedded in a slab gel for the second electrophoresis. However, the procedure described herein has the following advantages when compared to a procedure requiring physical manipulation of the first dimension gel: (a) reduction in the complexity of the experiment and reduction in the dexterity needed to achieve results, (b) assurance that the electrical field for the second electrophoresis is orthogonal to the field for the first electrophoresis, (c) reduction in differences between properties of gels used for the first and second electrophoresis. Because of the fragility of the 0.45% gel used in the analyses described by FIGS. 6A and 6B, the resultant data could have been obtained only with considerable difficulty with a procedure requiring manipulation of the first dimension gel.

The procedure demonstrated by the results shown in FIG. 5 identifies open circular and linear double-stranded DNA in a mixture known to contain only these two forms. From the data in Serwer et al. (Serwer, P. and Allen, J. L. (1984) Biochemistry 23, 922-927), it should also be possible to identify (by molecular weight and conformation) any component in a mixture containing only linear, open circular and closed circular DNA's. However, if either branched DNA's or DNA's that are either partially or totally single-stranded are present, it may become difficult to identify all DNA's by the use of a single two-dimensional electrophoresis (see Bell, L. and Byers, B. (1983) Anal. Biochem. 130, 527-535) for branched DNA). Further development will determine how much information can be obtained by two-dimensional electrophoresis of such a complex mixture. Multiple first dimensional gels 142, each with different gel concentrations, may be placed in a single second dimensional gel 144 and simultaneously used to provide additional information.

Because of the fragility of the gel used for the gel bed 142 in the first dimension electrophoresis in the analysis demonstrated by FIG. 5, the data so obtained cannot be obtained by any procedure that requires either handling or moving of the first dimension gel bed 142. Raising the agarose concentration of the first dimension gel bed 142 would decrease the separation of open circular DNA from the linear DNA's (Serwer, P. and Allen, J. L. (1984) Biochemistry 23, 922-927). Thus, the technique described relating to FIG. 5 is currently unique in its capacity for fractionating open circular DNA with a molecular weight of $26 \times 10^6$ (and larger). In addition, the precision in orthogonality of first dimension gel bed 142 and second electrical field is comparatively high. Except for band narrowing, the DNA bands after the second electrophoresis appear to have the same shape as DNA bands after one electrophoresis. In contrast, use of a two-dimensional procedure that requires manipulation of the first dimension gel results in bands that appear to have lost some of their outline (see, for example, FIGS. 6 and 7 in Bell, L. and Byers, B. (1983) Anal. Biochem. 130, 527-535). The greater the precision with which orthogonality of the two directions of electrophoresis is maintained, the better the preservation of band shape during two-dimensional electrophoresis.

The foregoing invention has been described in considerable detail, and it will be apparent to those skilled in the art that modifications and changes may be made in the procedure, materials utilized and in the apparatus 10 itself without departing from the concept and scope of the invention as described in the following claims.

What is claimed is:

1. An apparatus for conducting orthogonal electrophoretic analyses, the apparatus consisting essentially of:

a base;

a first pair of opposing tanks and a second pair of opposing tanks contained in said base, each tank comprising a buffer containment zone;

means for containing, on said base and between said tanks, a volume of liquid precursor gelling to form an open horizontal gel bed having four opposing edges, with an entire length of each edge being in communication with an adjacent buffer containment zone;

means for separating the buffer containment zones from an open horizontal gel bed formed from a volume of liquid precursor contained on the base, said means for separating comprising emplaceable barriers; and removable electrode assemblies adjustably attached to each tank for conducting electricity to each buffer containment zone, said removable electrode assemblies comprising an electrode having a length of an adjacent gel bed edge.

2. The apparatus of claim 1 wherein the means for containing is defined further as comprising a gel platen emplaceable on said base.

3. The apparatus of claim 2 wherein the gel platen is defined further as being cross-shaped.

4. The apparatus of claim 1 wherein the base is defined further as being able to hold a liquid to a level substantially immersing an open horizontal gel bed contained on said base and substantially filling the buffer containment zones.

5. The apparatus of claim 1 wherein the base is defined further as having walls, the means for containing is defined further as having an upper surface and the means for separating the buffer containment zones is defined further as comprising at least two blocks shaped to fittingly engage the base walls and the upper surface of the means for containing.

6. The apparatus of claim 1 wherein the tanks are defined further as having walls, a front rim and wall grooves adjacent to the front rim, and the means for separating the buffer containment zones is defined further as comprising slidable plates mounted in the wall grooves.

7. The apparatus of claim 1 wherein the tanks are defined further as having upper rims and the electrode assemblies are defined further as being removably and slidably attached to said upper rims.

8. The apparatus of claim 1 wherein the base is defined further as having a rim and the rim is defined further as having at least two vertically disposed guide pins.

9. The apparatus of claim 1 defined further as having a cover for inhibiting evaporation.

10. The apparatus of claim 1 wherein the base and tanks are defined further as comprising a unitary structure.

11. The apparatus of claim 1 wherein the means for separating the buffer containment zones is defined further as being electrically insulative.

12. The apparatus of claim 1 wherein the means for separating the buffer containment zones is defined further as preventing the flow of liquid between the buffer containment zones.

13. A process for conducting orthogonal gel electrophoresis of soluble materials consisting essentially of:
forming a horizontal open gel bed on the base of an apparatus having a first pair of opposing tanks and a second pair of opposing tanks, each tank comprising a buffer containment zone, the gel bed having four opposing edges with an entire length of each edge being in communication with an adjacent buffer containment zone;

supplying adjustable electrode assemblies for conducting electricity to each buffer containment zone;

providing means for separating the buffer containment zones from the horizontal open gel bed;

utilizing the means for separating to separate the buffer containment zones of the second pair of opposing tanks from the open horizontal gel bed;

immersing the horizontal open gel bed and the buffer containment zones in an electrophoresis buffer by addition of a sufficient amount of said buffer to the tanks;

emplacing a sample of soluble materials in the horizontal open gel bed adjacent to a buffer containment zone of the first pair of opposing tanks;

activating electrode assemblies to conduct a direct electrical current through the buffer containment zones of the first pair of opposing tanks to cause electrophoretic migration of the soluble materials a desired distance in a direction in the horizontal open gel bed between the activated electrode assemblies;

deactivating the electrode assemblies conducting a direct electrical current through the buffer containment zones of the first pair of opposing tanks;

utilizing the means for separating to separate the buffer containment zones of the first pair of opposing tanks from the open horizontal gel bed;

removing the separating means separating the buffer containment zones of the second pair of opposing tanks from the horizontal open gel bed and;

activating the electrode assemblies to conduct a direct electrical current through the buffer containment zones of the second pair of opposing tanks to cause electrophoretic migration of the soluble materials a desired distance in a direction in the horizontal open gel bed between the activated electrode assemblies.

14. A process for electrophoretically separating soluble substances comprising:
forming a laterally disposed gel bed with a first gel to include a trench extending in a first direction across the gel bed;

filling a portion of the length of said trench with a second gel to define a well proximate one end of said trench;

placing the soluble substances in liquid form in said well;

electrophoretically driving said substances said first direction through said second gel; and thereafter electrophoretically driving said substances from said second gel in a direction generally orthogonal to said first direction and into said first gel.

15. An apparatus for conducting orthogonal electrophoretic analysis of a soluble substance consisting essentially of:
a base having a flat surface adapted to support a horizontal open gel bed;

a first pair of tanks attached to the base and adapted to contain a liquid buffer in communication with the flat surface of said base and disposed on opposite sides in a first direction across the flat surface of said base;

a second pair of tanks attached to the base and adapted to contain a liquid buffer in communication with the flat surface of said base and disposed on opposite sides of said flat surface in a second direction, the second direction being orthogonal to the first direction;

separation barriers interposable between each of said tanks and the flat surface of the base to interupt communication there between when so interposed;

a removable template adapted to be placed on the flat surface of said base to define a trench in a horizontal open gel bed formed on the flat surface of said base;

a removable comb adapted to be placed on the flat surface of said base to define sample wells in a horizontal open gel bed formed on said flat surface;

separate electrode assemblies in each tank adapted to contact buffer contained in said tank and further adapted to be connected in a common electrical circuit with an opposing tank.

16. The apparatus of claim 15 wherein the flat base and said tanks constitute an integral structure.

17. An apparatus for conducting orthogonal electrophoresis of a soluble substance, the apparatus consisting essentially of:

a base comprising a baseplate with edges;

a first pair of opposing tanks adapted to contain a liquid buffer in communication with said baseplate and disposed on opposite sides of said baseplate in a first direction across said baseplate, each of said opposing tanks having an upper rim and a front rim, said front rim being connected to an edge of the baseplate;

a second pair of opposing tanks adapted to contain a liquid buffer in communication with said baseplate and disposed on opposite sides of said baseplate in a second direction which is orthogonal to the first direction, each of said opposing tanks having an upper rim and a front rim, said front rim being connected to an edge of the baseplate;

a gel platen with four edges and an upper surface, said gel platen being horizontally positionable on said baseplate so that each edge is adjacent to the front rim of a tank;

means for retaining a volume of a liquid gel precursor poured upon the gel platen and gelling to form an open horizontal gel bed, said means being emplaceable barriers, each of which fittingly engages an edge of the gel platen to separate an adjacent tank from the upper surface of the gel platen or formed horizontal gel bed;

an electrode assembly in each tank adapted to contact buffer contained in said tank and further adapted to be connected in a common electrical circuit with an electrode assembly of an opposing tank each electrode assembly being removably and slidably attached to the upper rim of a tank.

18. The apparatus of claim 17 wherein the juxtaposition of the tanks relative to the base is such that a bed of gel on the base can be covered by buffer overflowing from one or more of the tanks.

* * * * *